US007009069B2

(12) United States Patent
Valla et al.

(10) Patent No.: US 7,009,069 B2
(45) Date of Patent: Mar. 7, 2006

(54) INTERMEDIATES FOR USE IN RETINOID SYNTHESIS

(75) Inventors: Alain Valla, Loctudy (FR); Dominique Cartier, Quimper (FR); Roger Labia, Plougonnec (FR); Pierre Jean-Paul Potier, Paris (FR)

(73) Assignee: Centre National de la Recherche Scientifique (C.N.R.S.), (FR)

( * ) Notice: Subject to any disclaimer, the term of this patent is extended or adjusted under 35 U.S.C. 154(b) by 66 days.

(21) Appl. No.: 10/399,910

(22) PCT Filed: Oct. 26, 2001

(86) PCT No.: PCT/FR01/03331

§ 371 (c)(1),
(2), (4) Date: Apr. 24, 2003

(87) PCT Pub. No.: WO02/34710

PCT Pub. Date: May 2, 2002

(65) Prior Publication Data

US 2004/0132796 A1    Jul. 8, 2004

(30) Foreign Application Priority Data

Oct. 26, 2000 (FR) ................... 00 13726

(51) Int. Cl.
*C07C 229/20* (2006.01)
(52) U.S. Cl. ...................... 560/171; 560/172
(58) Field of Classification Search ............. 560/171, 560/172
See application file for complete search history.

(56) References Cited

U.S. PATENT DOCUMENTS

| 4,195,999 | A | 4/1980 | Adachi et al. ............ 430/507 |
| 5,925,797 | A | 7/1999 | Giraud et al. ............ 568/446 |

FOREIGN PATENT DOCUMENTS

| DE | 1 046 612 | 12/1958 |
| DE | 1 559 900 | 6/1959 |
| DE | 28 16 226 | 10/1978 |
| EP | 0 802 180 | 10/1997 |
| FR | 1 055 849 | 2/1954 |

OTHER PUBLICATIONS

Bull. Acad. Sci. USSR Div. Chem. Sci., vol. 39, No. 2.1, 1990, pp. 298-306.
Bull. Acad. Sci. USSR Div. Chem. Sci., vol. 24, 1975, pp. 2397-2401.
Chem. Heterocycl. Compd., vol. 24, No. 10, 1988, pp. 1095-1103.
Journal of the American Chemical Society, vol. 116, No. 6, 1994, pp. 2619-2620.
Journal of the American Chemical Society, vol. 115, No. 7, 1993, pp. 3006-3007.
Ber. Bunsen-Ges. Phys. Chem., vol. 80, 1976, pp. 630-636.
Pharmazie, vol. 54, No. 8, 1999, pp. 571-574.
Journal of Organic Chemistry, vol. 64, No. 26, 1999, pp. 9493-9498.
Bull. Acad. Sci. USSR Div. Chem. Sci., vol. 22, 1973, pp. 2478-2482.
Bull, Acad. Sci. USSR Div. Chem. Sci. vol. 22, 1973, pp. 1963-1971.
Ivz. Akad. SSSR, 1972, pp. 2153-2218.
Bull. Acad. Sci. USSR Div. Chem. Sci., vol. 29, 1980, pp. 1643-1651.
Bull. Acad. Sci. USSR Div. Sci., vol. 30, No. 2, 1981, pp. 308-311.

*Primary Examiner*—Taofiq Solola
(74) *Attorney, Agent, or Firm*—Steptoe & Johnson LLP

(57) ABSTRACT

The invention concerns compounds of formula (1) wherein in particular G represents the $-N(CH_3)_2-$, $-N(C_2H_5)_2-$ group or N-pyrrolidine: n is an integer equal to 1 or 2: $R_1$, $R_2$ and $R_3$, independently of one another, represent a hydrogen atom or a methyl group, the successive unsaturated units capable of being moreover identical or different, provided that at least one of the substituents $R_1$, $R_2$ and $R_3$ is different from H; and $Y_1$ and $Y_2$ represent each a $-COOCH_3$ group or a $-COOC_2H_5$ group.

1 Claim, No Drawings

INTERMEDIATES FOR USE IN RETINOID SYNTHESIS

The subject of the present invention is novel intermediates which are useful for the synthesis of retinoids and carotenoids, and their preparation. It also relates to a novel method for the synthesis of retinoids, in particular retinoic acid and vitamin A or retinol via the retinoic acid thus obtained.

Retinoids, in particular vitamin A, are used in various fields, in particular in the therapeutic field, the cosmetic field and in the agro-foodstuffs sector and many methods of synthesis have been used.

Many methods of preparation have been used for the synthesis of retinoids, in particular for that of retinoic acid and vitamin A and a recent article relating to industrial techniques which make it possible to obtain vitamin A has been described by Paust J. (Pure & Appl. Chem. (1991), 63, 45–58).

The first synthesis of retinoids belonging to the vitamin A family was described by R. Kuhn and C. J. O. R. Morris (Ber. (1937), 70, 853).

The condensation of β-ionylideneacetaldehydes with ethyl 3-methylcrotonate leads to different retinoic acids, depending on the configuration of the aldehyde, the nature of the solvent and the base used for generating the anion (M. Matsui, S. Okano K. Yamashita, M. Miyano, S. Kitamura, A. Kobayashi, T. Sato and B. R. Mikami *J. Vitaminol.* (Kyoto), (1958), 4, 178).

These same isomers have been synthesized by a similar route from various C-15 aldehydes and methyl β-methylglutaconates (C. D. Robeson, J. D. Cawley, L. Weisler, M. H. Stern, C. C. Eddinger and A. J. Chechak, *J. Am. Chem. Soc.* (1955), 77, 4111).

The synthesis of 13Z-retinoic acid has also been carried out by a Réformatskii reaction between the C-15 aldehyde and methyl γ-bromo-β-methylcrotonate (Eiter, E. Truscheit and H. Oediger, *Angew. Chem.* (1960), 72, 948).

The reduction of the various C-20 methyl esters, with LiAlH$_4$, leads to the corresponding isomers of vitamin A. Retinal is obtained from the latter by oxidation (U.S. Pat. No. 3,367,985; J. D. Surmatis, S. Ball, T. W. Goodwin at R. A. Morton, *Biochem. J.* (1948), 42, 516; C. D. Robertson, W. P. Blum, J. M. Dieterle, J. D. Cawley and J. G. Baxter *J. Am. Chem. Soc.* (1995), 77, 4120).

Similarly, the α vitamin A derivatives were prepared by condensation of ethyl 3-methylcrotonate with α-ionylideneacetaldehyde (P. S. Marchand, R. Rüegg, U. Schwieter, P. T. Siddons and B. C. L. Weddon, *J. Chem. Soc.* (1965), 2019).

The Wittig and Horner reactions, starting with the C-15 aldehyde, have been widely used for the synthesis of many vitamin A derivatives.

Thus, the esters of retinoic acid have been prepared using:
  the phosphonium salt derived from methyl γ-bromo-β-methylcrotonate (patent DE 950 552; G. Wittig and H. Pommer, *Chem. Abstr.* (1959), 53, 436), and
  the phosphonate equivalent (H. Pommer, *Angew. Chem.* (1960), 72, 811).

Retinonitrile and acetate of vitamin A have been prepared using:
  the phosphonium salt derived from γ-bromo-β-crotonitrile (H. Pommer, *Angew. Chem.* (1960), 72, 811), and
  the corresponding phosphonate (patent DE 1 116 652; H. Pommer and W. Stilz, *Chem. Abstr.* (1962), 57, 2267).

Retinal has also been synthesized by:
  a Wittig reaction with (4,4-diethoxy-2-methyl-2-butenyl)triphenylphosphonium bromide,
  condensation of the diethyl acetal of β-ionylideneacetaldehyde with 1-ethoxy-3-methyl-1,3-butadiene (S. M. Makin, *Russ. Chem. Rev.* (Engl. Transl.) (1969), 38, 237), and
  oxidation according to Oppenauer of a mixture of β-ionylideneethanol and β,β-dimethylallyl alcohol (patent JP 5145/58; M. Matsui and S. Kitamura, *Chem. Abstr.* (1959), 53, 17, 178).

The method developed by H. Pommer (*Angew. Chem.* (1960), 72, 811), currently used by the company Badische Anilin & Soda Fabrik AG (BASF) uses a Wittig reaction between (β-ionylideneethyl)triphenylphosphonium chloride and γ-acetoxytiglaldehyde, in the presence of sodium methoxide. The reaction product consists of a mixture of all-E and 11Z acetates from which the all-E isomer is obtained by crystallization (patent DE 1 058 710; H. Pommer and W. Sarnecki, *Chem. Abstr.* (1961), 55, 12, 446; patent DE 1 046 612; H. Pommer and W. Sarnecki, *Chem. Abstr.* (1961), 55, 5573 and patent DE 1 059 900; H. Pommer and W. Sarnecki, *Chem. Abstr.* (1961), 55, 14, 511).

Retinoic acid and the corresponding ethyl ester have been synthesized by the same route by respectively substituting β-formylcrotonic acid or ethyl β-formylcrotonate for γ-acetoxytiglaldehyde (patent DE 1 058 710; H. Pommer and W. Sarnecki, *Chem. Abstr.* (1961), 55, 12, 446; patent DE 1 046 612; H. Pommer and W. Sarnecki, *Chem. Abstr.* (1961), 55, 5573; patent DE 1 059 900; H. Pommer and W. Sarnecki, *Chem. Abstr.* (1961), 55, 14, 511; patent DE 1 068 702; H. Pommer and W. Sarnecki, *Chem. Abstr.* (1961), 55, 10, 812).

9Z-retinoic acid was prepared from the C-15 phosphonium salt derived from β-(Z)-ionylideneethanol (patent DE 1 068 710; H. Pommer and W. Sarnecki, *Chem. Abstr.* (1961), 55, 12, 446). Thus, the synthesis of retinoic acid (and its esters) which is industrially used by BASF uses a Wittig reaction between phosphorane and a C-5 aldehyde (H. Pommer and W. Sarnecki, already cited), said phosphorane being synthesized by the action of triphenylphosphine on β-ionol.

The first stereoselective synthesis of 11Z, 13Z-retinoic acid was carried out in 1965 by Pattenden et al., by the Wittig reaction between phosphorane (generated from β-ionylideneethyltriphenylphosphonium bromide) and 4-hydroxy-3-methyl-2-buten-4-olide (G. Pattenden, B. C. L. Weedon, C. F. Garbers, D. F. Schneider and J. P. van der Merwe, *Chem. Commun.* (1965) 347). The reaction mixture changes, leading to a mixture of retinoic acids which can be separated by fractional crystallization. Controlled isomerization of 11Z,13Z-retinoic acid leads respectively to 13Z- or all-E-retinoic acids (G. Pattenden and B. C. L. Weedon, *J. Chem. Soc. C* (1968), 1984; C. F. Garbers, D. F. Schneider and J. P. van der Merwe, *J. Chem. Soc. C* (1968), 1982).

A similar approach, described by G. Cainelli and G. Cardillo (*Acc. Chem. Res.* (1981), 14, 89) and G. Cainelli, G. Cardillo, M. Contendo, P. Grasselli and A. Umani Ronchi (*Gazz. Chim. Ital.* (1973), 103, 117) uses the reaction of dienolate (derived from the sodium salt of senecioic acid) on the C-15 aldehyde.

Alternatively, R. W. Dugger and C. H. Heathcock (*J. Org. Chem.*, (1980), 45, 1181) prepared lactones by the action of the dienolate (derived from ethyl senecioate) on E- and Z-β-ionylideneacetaldehyde.

G. Cardillo, M. Contendo and S. Sandri, (*J. Chem. Soc. Perkin I* (1979), 1729) have proposed a stereospecific synthesis of all-trans-retinal via β-ionylideneacetaldehyde and the dianion derived from 3-methyl-3-butenol.

The preparation of vitamin A and that of the ethyl ester of retinoic acid were also carried out by condensation of methyl β-formylcrotonate with the C-15 Grignard derivatives (K. K. Chugai Seiyaku *Derwent Farmdoc* (1964), 11, 643; K. Shishido, H. Nozaki and M. Tsuda, *Derwent Farmdoc*, (1964), 11, 669).

The condensation of the bis(2,2,2-trifluoroethyl)phosphonate anion (generated by potassium hexamethyldisilazide/18-crown-6) with 7Z,9Z-β-ionylideneacetaldehyde leads to the mixture of the 7Z,9Z-, 7Z,9Z,11Z-, 7Z,9Z,13Z- and 7Z,9Z,11Z,13Z-retinonitriles, which may be separated by high-performance liquid chromatography (HPLC) (A. Trehan, T. Mirzadegan and R. S. H. Liu, *Tetrahedron*, (1990), 46, 3769; W. C. Still and C. Gennari, *Tetrahedron Lett.* (1983), 24, 4405).

Other authors used the benzoic ester of 7Z-ethynylcarbinol to prepare 11Z-18,14-retroretinol. The photochemical isomerization of ethynyl-β-ionol made it possible to obtain the compound possessing a C-7 Z configuration (Y. S. Chauhan, R. A. S. Chandraratna, D. A. Miller, R. W. Kondrat, W. Reischl and W. H. Okamura, *J. Am. Chem. Soc.* (1985), 107, 1028). The hydrolysis of benzoate with a base, such as for example 1,8-diazabicyclo[5.4.0]undec-7-ene (DBU), allows the formation of the retrosystem.

The condensation of the C-15 aldehyde of E configuration, with diethyl isopropylidenemalonate followed by the hydrolysis of the ester, gave 14-carboxyretinoic acid (Y. F. Shealy, C. A. Krauth, J. M. Riodan and B. P. Sani, *J. Med. Chem.* (1988), 31, 1124).

The condensation of β-ionylideneacetaldehyde, dimethylacetal with trimethylsilyldienol ether or ethyl-dienol ether, catalyzed by a Lewis acid, gives the mixture of 11-methoxy- and 11,12-dihydroretinals which, by removal of methanol under the action of a base followed by isomerization ($I_2$), produces the all-trans-retinal (T. Mukaiyama and I. Ishida *Chem. Lett.* (1975), 1201).

M. Julia and D. Arnould (*Bull. Soc. Chim. Fr.* (1973), 746) have reported a stereoselective synthesis in which the tetraenic chain is generated by alkylation via a sulfinic acid, followed by removal of said acid.

This synthesis has been repeated by the companies Hoffmann-La Roche (P. S. Manchand, M. Rosenberg, G. Saucy, P. A. Wehrli, H. Wong, L. Chambers, M. P. Ferro and W. Jackson, *Helv. Chim. Acta* (1976), 59, 387) and Rhône Poulenc Industries (P. Chabardes, J. P. Décor and J. Varagnat, *Tetrahedron Lett.* (1977), 33, 2799) for the production of vitamin A in the all-trans form and of the corresponding acetate (for the latter, starting with C-5 chloroacetate). The stereoselectivities being from 9E:9Z≈73:27 to 82:18.

Olson et al. have described a preparation of all-trans-vitamin A (in acetate form), starting with all-trans C-15 bromotriene, prepared from vinyl-β-ionol, and C-5 tolyl sulfone (G. L. Olson, H. C. Cheung, K. D. Morgan, C. Neukom and G. Saucy *J. Org. Chem.* (1976), 41, 3287). Manchand et al. report a sequence using another unit in C-5, with the C-15 sulfone, for the synthesis of retinyl acetate. The π complex of allylpalladium/prenyl acetate is stereoselectively alkylated at the δ position with the anion of the sulfone (P. S. Manchand, H. S. Wong and J. F. Blount *J. Org. Chem.* (1978), 43, 4769∝74).

By photoisomerization of these compounds, it is possible to obtain the 7Z;7Z, 11Z;7Z, 13Z;7Z,9Z,11Z and all-Z isomers (R. S. H. Liu and A. E. Asato *Tetrahedron Lett.* (1984), 40, 1931).

A recent synthesis also makes it possible to prepare the 13Z and 13E-retinoic acids by the use of novel synthons β-methylenealdehydes, by condensation according to Stobbe with methyl isopropylidenemalonate, in the presence of Triton B (Patent Application EP 0 802 180; Giraud M. et al.).

Currently, the three main industrial syntheses use β-ionone as starting material.

The Hoffmann-La Roche strategy is derived from the Isler technique (O. Isler, W. Huber, A. Ronco and M. Kofler *Helv. Chim. Acta* (1947), 30, 1911; O. Isler, A. Ronco, W. Guex, N. C. Hindley, W. Huber, K. Dialer and M. Kofler, *Helv. Chim. Acta* (1949), 32, 489) and uses a synthon in C-14 and a synthon in C-6.

The synthon in C-6 which is used is itself prepared in 3 steps.

Another industrial synthesis developed by Badische Anilin & Soda Fabrik AG (BASF) is based on the method of Inhoffen and Pommer (H. Pommer *Angew. Chem.* (1960), 72, 811).

The synthon used for the extension of the chain is prepared in 4 steps.

The synthesis of vitamin A carried out by Rhône Poulenc Rorer (RPR) is adapted from the Julia technique (Julia M. and Arnould D. *Bull. Soc. Chim.* (1973), 746).

In this method, a synthon in C-6 prepared in 4 steps is used.

All the industrial methods recalled above use dangerous and/or toxic reagents, in particular sodium in liquid ammonia, organometallics, aluminum hydrides, phosphorus oxychloride, chlorine and pyridine; they also require the use of catalytic hydrogenation steps which are particularly dangerous. The preparation of the synthons comprises several steps and all these methods require, in addition, the use of purification steps in order to remove by-products, which makes these methods long and expensive.

Given the importance of retinoids and the derivatives thereof, in particular that of retinoic acid and vitamin A, it is essential to find methods of synthesis which overcome or limit these disadvantages.

Accordingly, the inventors set themselves the objective of synthesizing compounds which are useful as intermediates in the synthesis of retinoids and of their derivatives, in particular in that of retinoic acid and of vitamin A, which are easy to use.

The subject of the present invention is compounds of formula (1)

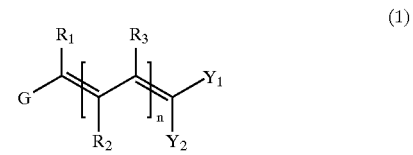
(1)

in which
G represents:
either a halogen atom,
or a group —$NR_4R_5$ where $R_4$ and $R_5$, which are identical or different, are each a linear or branched alkyl group (of 1 to 5 carbon atoms), or a substituted or unsubstituted, saturated or unsaturated cycloalkyl group (of 3 to 7 carbon atoms), or a substituted or unsubstituted aryl group, or $R_4$ and $R_5$ form a ring with the nitrogen atom carrying them,
or a group OP where P is a group protecting the hydroxyl functional group, provided that OP is not included in a bond where $Y_1$ or $Y_2$,
or a group SR, SOR or $SO_2R$ where R is a linear or branched alkyl group (of 1 to 5 carbon atoms) or a substituted or unsubstituted, saturated or unsaturated cycloalkyl group (of 3 to 7 carbon atoms), or a substituted or unsubstituted aryl group, $R_1$ represents:
either a hydrogen atom,
or a linear or branched alkyl group (of 1 to 5 carbon atoms), n is an integer between 1 and 6, $R_2$ and $R_3$ represent identical or different substituents in each of the unsaturated units, it being possible moreover for said successive unsaturated units to be identical or different, $R_2$ and $R_3$ being chosen from the group comprising hydrogen, linear or branched alkyl groups (of 1 to 5 carbon atoms), and aryl groups, it being possible for said alkyl and aryl groups to be substituted, provided that at least one of the substituents $R_1$, $R_2$ and $R_3$ is different from H, at least one of $Y_1$ and $Y_2$ represents a group —$COOR_7$ and the other is chosen from the group comprising the groups —$COR_6$, —CN, —$COOR_7$, —$CONR_8R_9$ where $R_6$ and $R_7$ are each an alkyl group (of 1 to 5 carbon atoms) and $R_8$ and $R_9$ are each a linear or branched alkyl group (of 1 to 5 carbon atoms), with the exception of the following compounds of formula (1) where n=1 and:

$R_1$=$CH_3$, $R_2$=$R_3$=H, G=N $(CH_3)_2$, $Y_1$=$COOCH_3$, $Y_2$=$COCH_3$.
$R_1$=$CH_3$, $R_2$=$R_3$=H, G=N $(C_2H_5)_2$, $Y_1$=$COOCH_3$, $Y_2$=$COCH_3$.
$R_1$=$CH_3$, $R_2$=$R_3$=H, G=N $(C_2H_5)_2$, $Y_1$=$COOC_2H_5$, $Y_2$=$COCH_3$.
$R_1$=H, $R_2$=$CH_3$, $R_3$=H, G=$OCH_3$, $Y_1$=$Y_2$=$COOCH_3$.
$R_1$=H, $R_2$=$CH_3$, $R_3$=H, G=$OC_2H_5$, $Y_1$=$Y_2$=$COOCH_3$.
$R_1$=H, $R_2$=$CH_3$, $R_3$=H, G=$OC_2H_5$, $Y_1$=$Y_2$=$COOC_2H_5$.
$R_1$=H, $R_2$=$CH_3$, $R_3$=H, G=N $(CH_3)_2$, $Y_1$=$Y_2$=$COOCH_3$.
$R_1$=H, $R_2$=$CH_3$, $R_3$=H, G=N $(CH_3)_2$, $Y_1$=$COOCH_3$, $Y_2$=$COCH_3$.
$R_1$=H, $R_2$=$CH_3$, $R_3$=H, G=N $(CH_3)_2$, $Y_1$=$COOCH_3$, $Y_2$—CN.
$R_1$=H, $R_2$=$CH_3$, $R_3$=H, G=pipéridyl, $Y_1$=$COOC_2H_5$, $Y_2$=CN.
$R_1$=H, $R_2$=$CH_3$, $R_3$=H, G=N $(CH_3)_2$, $Y_1$=$COOC_2H_5$, $Y_2$=$COC_6H_5$.
$R_1$=H, $R_2$=$C_2H_5$, $R_3$=H, G=$OC_2H_5$, $Y_1$=$Y_2$=$COOC_2H_5$.
$R_1$=H, $R_2$=iso-propyl, $R_3$=H, G=N $(CH_3)_2$, $Y_1$=$Y_2$=$COOCH_3$.
$R_1$=H, $R_2$=iso-propyl, $R_3$=H, G=N $(CH_3)_2$, $Y_1$=$COOCH_3$, $Y_2$=$COCH_3$.
$R_1$=H, $R_2$=iso-propyl, $R_3$=H, G=N $(CH_3)_2$, $Y_1$=$COOC_2H_5$, $Y_2$=$COC_6H_5$.
R=$R_2$=H, $R_3$=$CH_3$, G=$OC_2H_5$, $Y_1$=$COOC_2H_5$, $Y_2$=CN.
R=$R_2$=H, $R_3$=$CH_3$, G=N $(CH_3)_2$, $Y_1$=$COOC_2H_5$, $Y_2$—CN.

and with the exception of the compound of formula (1) where n=2 of the following formula methyl (2-acetyl-7-(dimethylamino)-4-methyl-2,4,6-heptatrienoate:

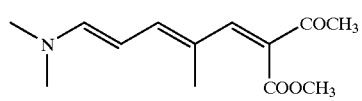

For the purposes of the present invention, the expression halogen is understood to mean in particular iodine, bromine, chlorine and fluorine.

For the purposes of the present invention, the expression aryl group is understood to mean a benzene or bicyclic ring. By way of nonlimiting example, there may be mentioned the phenyl and naphthyl groups, it being possible for said groups to be substituted.

For the purposes of the present invention, the expression cycloalkyl group is understood to mean a ring of 1 to 7 carbon atoms, saturated or containing one or two unsaturations, optionally substituted with one or more alkyl groups (of 1 to 4 carbon atoms). By way of nonlimiting example, there may be mentioned the 2,6,6-trimethylcyclohexenyl and 2,6,6-trimethlcyclohexadienyl groups.

For the purposes of the present invention, the expression group protecting the hydroxyl functional group is understood to mean groups such as those defined by T. W. Greene in "*Protective groups in organic synthesis*" (John Wiley Interscience, Ed. $2^{nd}$ Ed., 1991). By way of nonlimiting example, there may be mentioned alkyl ethers, silylated ethers, phosphorus-containing ethers, esters, carbonates and sulfonates.

Compounds having a similar structure corresponding to formula (1) for which n=0 are known and described in the literature.

Thus, the unsubstituted monoethylenic derivative (1-a)

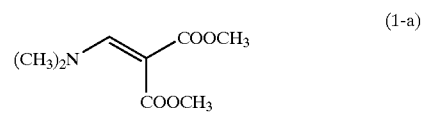

has been synthesized by several authors, in particular by Sorsak G., Grdadolnik S. and Stanovnik B. (*Ach. Mod. Chem.* (1998), 135, 613–24) from dimethylformamide dimethyl acetal (DMFDMA).

The unsubstituted monoethylenic derivative (1-b)

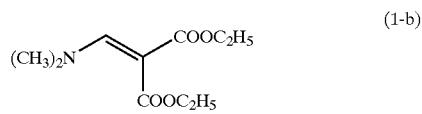

has been synthesized by Regitz M. and Himbert G. (*Justus Liebigs Ann. Chem.* (1970), 734, 70–85) and more recently by Gabbutt C., Hepworth J., Heron B., Elsegood M. and Clegg W. (*Chem. Commun.* (1999), 3, 289–90).

Some compounds of formula (1) where n=1 are also known and described in the literature.

The synthesis of the unsubstituted diethylenic derivative (1-c) has been described by Krasnaya Zh. et al. (*Bull. Acad. Sci. USSR Div. Chem. Sci., Engl. Transl.* (1973), 22, 1959–62)

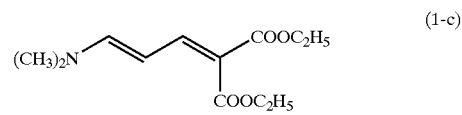

The synthesis of the substituted diethylenic derivatives (1-d) where R and R' represent in particular alkyl or aryl groups has been described by Smetskaya N. I., Mukhina N. A. and Granik V. G. (*Chem. Heterocycl. Compd.*, Engl Transl. (1984), 20, 650–53) and Michalik M., Zahn K., Köeckritz P. and Liebscher J. (*J. Prakt. Chem.* (1989), 331, 1–10; *Bull. Acad. Sci. USSR Div. Chem. Sci. Engl. Transl.* (1973), 22, 1959–62)

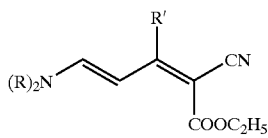
(1-d)

These same authors also describe compounds (1-e) where R, R' and R" represent in particular alkyl or aryl groups.

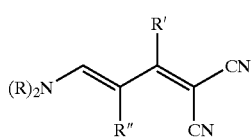
(1-e)

However, the compounds (1-d) and (1-e) have never been used in the synthesis of retinoids.

The unsubstituted monoethylenic derivative (1-f)

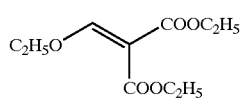
(1-f)

has been widely described and used, in particular for the synthesis of the corresponding enamines or of heterocycles (Yamashkin S. and Yurovskaya M. *Chem. Heterocycl. Compd., Engl. Transl.* (1997), 33, 1284–87; Glushkov R., Vozyakova T., Adamskaya E., Gus'kova T. et al. *Pharm. Chem. J., Engl. Transl.*, (1998), 32, 8–12; Kim Y., Kwon T., Chung S. and Smith M. *Synth. Commun.* (1999), 29, 343–50).

The unsubstituted diethylenic derivative (1-g)

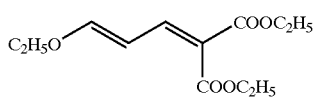
(1-g)

has been synthesized in particular by Engel C. et al. *Can. J. Chem.* (1973), 51, 3263–71; Overman L. and Robichaud A. *J. Am. Chem. Soc.* (1989), 111, 300–308; Krasnaya Zh., Stytsenko T. and Bogdanov V. *Bull. Acad. Sci. USSR Div. Chem. Sci., Engl. Transl.* (1990), 39, 2316–21; Gelin R. and Makula D. *Bull. Soc. Chim. Fr.* (1968), 1129–35; de Bie D., Geurtsen B., Berg I., and van der Henk C. *J. Org. Chem.* (1896), 51, 3209–11.

The synthesis of the unsubstituted diethylenic derivative (1-h) has also been described by Shramoya Z. et al. (*J. Org. Chem. USSR* (*Engl. Transl.*) (1966), 2, 1005–1009) and by Gelin R. and Makula D. (*Bull. Soc. Chim. Fr.* (1968), 1129–35)

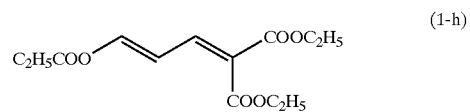
(1-h)

The dimethyl derivative (1-x)

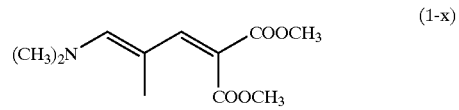
(1-x)

has been synthesized by Bogdanov et al., *Bull. Acad. Sci. USSR Div. Chem. Sci.* (Engl. Transl.) (1990), 39, 298–306 and 1172–80.

However, the compounds (1-f) to (1-h) and (1-x) have never been used in the synthesis of retinoids.

In a particular embodiment of the invention, the compounds of formula (1) are those for which:

G represents a group —$NR_4R_5$ where $R_4$ and $R_5$, which are identical or different, are each a linear or branched alkyl group (of 1 to 5 carbon atoms), or a cycloalkyl group (of 3 to 7 carbon atoms), or $R_4$ and $R_5$ form a ring with the nitrogen atom carrying them, $R_1$ represents either a hydrogen atom or a linear or branched alkyl group (of 1 to 5 carbon atoms), n is an integer between 1 and 2, $R_2$ and $R_3$ represent a similar or different substituent in each of the unsaturated units, it being possible moreover for said successive unsaturated units to be identical or different, $R_2$ and $R_3$ being chosen from the group comprising hydrogen and the linear or branched alkyl groups (of 1 to 5 carbon atoms), and provided that at least one of the substituents $R_1$, $R_2$ and $R_3$ is different from H, and $Y_1$ and $Y_2$ each represent a group —$COOR_7$ where $R_7$ is an alkyl group (of 1 to 5 carbon atoms).

In another particular embodiment, the compounds of formula (1) are those for which, G represents the group —$N(CH_3)_2$, —$N(C_2H_5)_2$ or N-pyrrolidine, n is an integer equal to 1 or 2, $R_1$, $R_2$ and $R_3$ represent, independently of each other, a hydrogen atom or a methyl group, it being possible moreover for the successive unsaturated units to be identical or different, provided that at least one of the substituents $R_1$, $R_2$ and $R_3$ is different from H, and $Y_1$ and $Y_2$ each represent a group —$COOCH_3$ or a group —$COOC_2H_5$.

In an advantageous embodiment according to the invention, the compounds are chosen from the group consisting of:

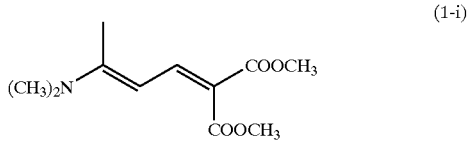
(1-i)

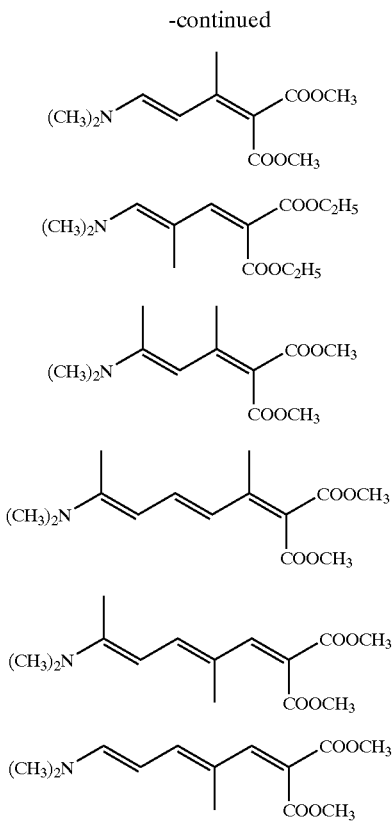

and the ethyl ester analogs of the compounds (1-i) to (1-j) and (1-l) to (1-o).

The compounds according to the invention may be prepared by techniques known to persons skilled in the art, starting with products of formula (3)

$$\underset{R_2\ \ Y_2}{\overset{R_1\ \ \ R_3}{R-\!\!\!=\!\!\!=\!\!\!\left[\ \right]_n\!\!\!-\!\!Y_1}}$$
(3)

in which $R_1$, $R_2$ and $R_3$, $Y_1$ and $Y_2$ are as defined above and R represents an alkyl group (of 1 or 2 carbon atoms), which are commercially available or which can be obtained by methods described in the literature, or by the method described in the present application.

Thus, the compound (1-j) may be prepared by reacting the methyl isopropylidenemalonate of formula (3-a) (n=0, $R=R_1=CH_3$ and $Y_1=Y_2=$—$COOCH_3$).

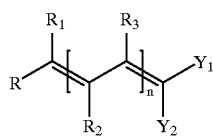
(3-a)

with a protected form of N,N-dimethylformamide, for example dimethyl acetal, of formula (2-a) or DMFDMA

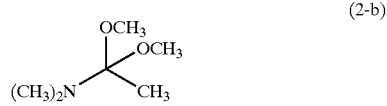
(2-a)

Likewise, the compounds 1-i, 1-l, 1-m and 1-n, according to the invention, may be prepared from N,N-dimethylacetamide dimethyl acetal of formula (2-b)

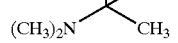
(2-b)

The compounds of formula (1), in which G represents a group —$NR_4R_5$ where $R_4$ and $R_5$ are as defined above, may be obtained in a manner similar to those used in the scheme which follows:

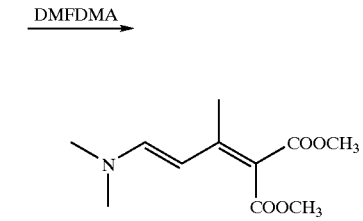
(3-a) → (1-j)

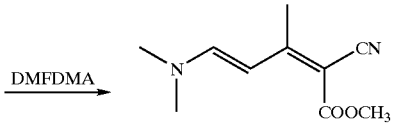
(3-b) → (1-q)

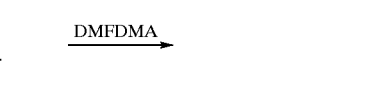
(3-c)

(1-p)

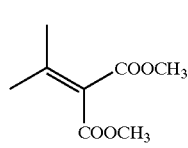

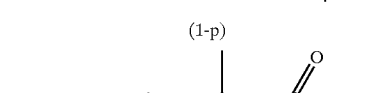
(1-t)

-continued

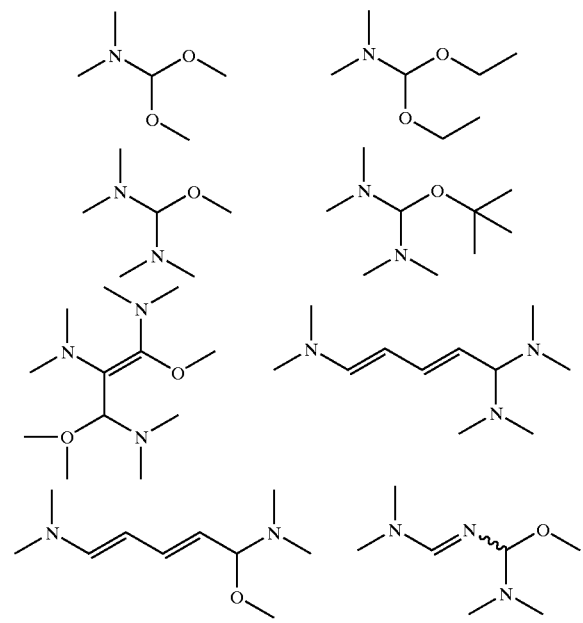

Other protected forms of N,N-dimethylformamide or equivalent derivatives, which are suitable for use, may be chosen from the group consisting of:

the complex: N,N-dimethylformamide-dimethylsulfate; they can also be prepared by the simultaneous or successive action of ethyl or methyl orthoformate or of ethyl or methyl orthoacetate and of a secondary amine $HNR_4R_5$.

Moreover, the compounds of formula (1) with $R_1=R_2=H$ and $R_3=CH_3$ may be prepared by reacting acetylacetaldehyde dimethyl acetal with a compound possessing a diactivated methylene, in the presence of a secondary amine, according to the following scheme

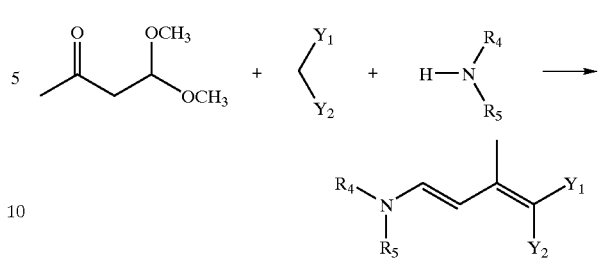

$Y_1$, $Y_2$, $R_4$ and $R_5$ are as defined above.

The subject of the present invention is also a method for synthesizing a compound of formula (1) comprising n+1 units from a compound (1) comprising n units, characterized in that an organometallic such as, for example, an alkyl- or arylmagnesium halide or an alkyl- or aryllithium is reacted, in a solvent such as, for example, tetrahydrofuran (THF), dimethoxyethane (DME), ethyl ether and tert-butyl methyl ether, with a compound of formula (1) comprising n units, in order to obtain a compound of formula (3) which is treated with a compound of formula (2) and a compound of formula (1) comprising n+1 units is obtained.

In the case where n=1, then the method may be illustrated by the scheme which follows:

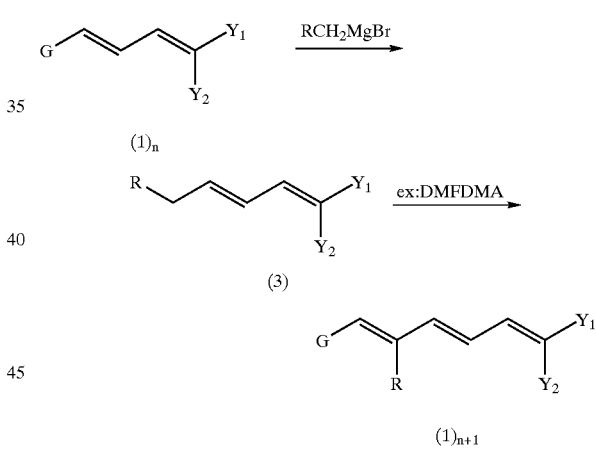

The subject of the present invention is also a method for synthesizing a compound of formula (1) comprising n+2 units from a compound of formula (1) comprising n units, characterized in that the compound of formula (1) comprising n units is reacted, in a solvent such as, for example, tetrahydrofuran (THF), dimethoxyethane (DME), ethyl ether and tert-butyl methyl ether, with the enolate of a ketone, preferably acetone or butanone, said enolate being generated by a base such as, for example, sodium hydride, lithium diisopropylamide, and then an organometallic such as, for example, an alkyl- or arylmagnesium halide or an alkyl- or aryllithium is added, and the compound of formula (3) obtained is treated with a compound of formula (2) and a compound of formula (1) comprising n+2 units is obtained.

In the case where n=1, then the method may be illustrated by the scheme which follows:

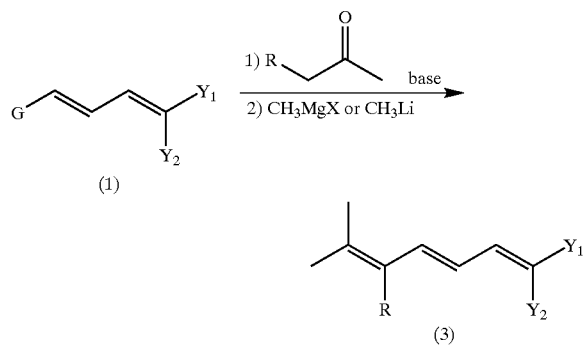

(1)

(3)

The subject of the present invention is also a method for preparing an aldehyde of formula (4)

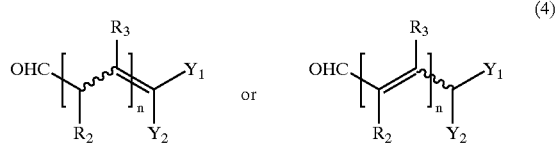

(4)

in which $R_2$, $R_3$, $Y_1$ and $Y_2$ are as defined above, characterized in that a compound of formula (1) is caused to react preferably in an aqueous acidic medium (in particular 1 to 2 M HCl) or in formic acid in a heterogeneous phase.

In the case where n=1, said method may be illustrated by the following scheme:

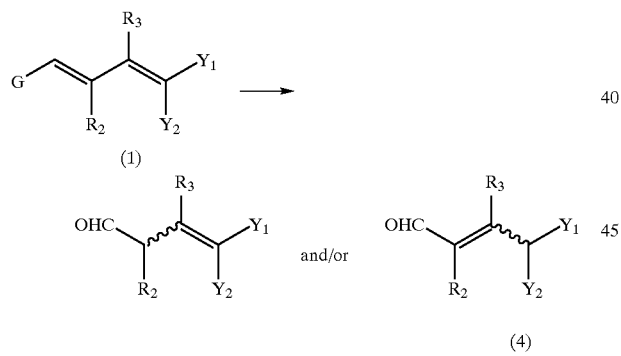

(1)

and/or (4)

The subject of the present invention is also a method for synthesizing retinoids, characterized in that a compound of formula (1) is used as intermediate.

In a particular embodiment of said method, it comprises at least one step consisting in reacting a compound of formula (1) with a compound of formula (5)

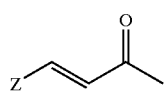

(5)

in which Z is chosen from the group comprising the following radicals:

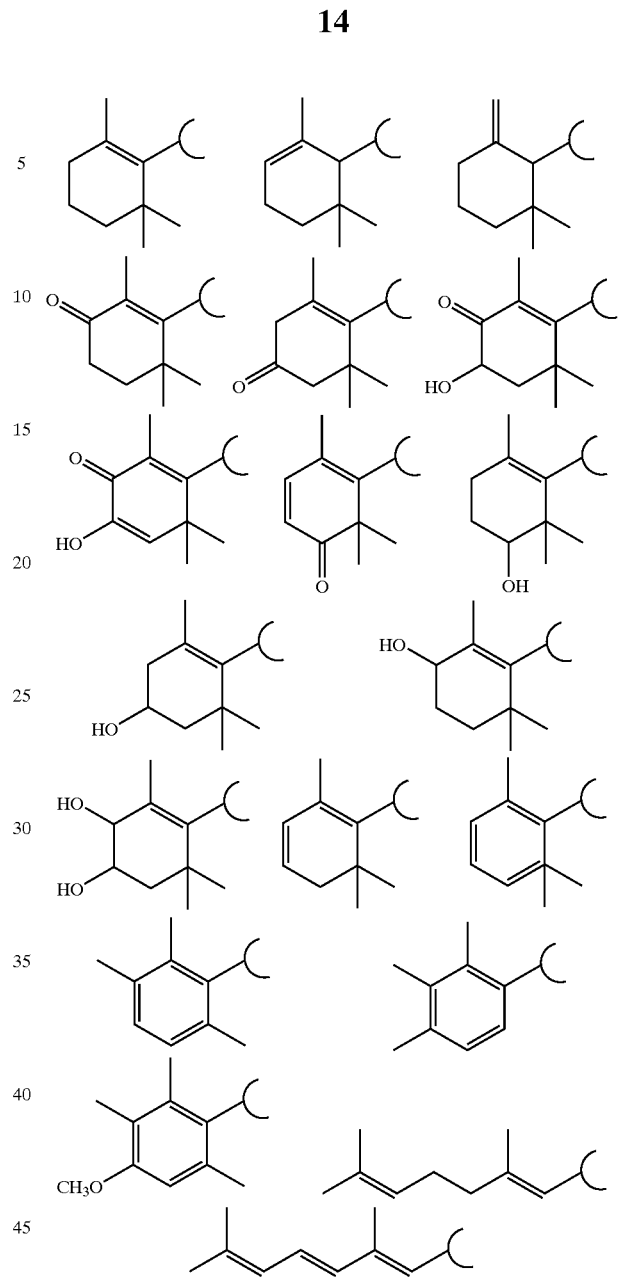

In a particular embodiment of the invention, the synthesis is carried out in the presence of a base, preferably chosen from the group consisting of alkali metal amides, hydrides and alcoholates.

In the case where Z contains an oxygenated functional group (CO, HO and the like), a protected form of this functional group (as defined in *Protective Groups in Organic Synthesis* (T. W. Greene, $2^{nd}$ Ed., (1991), Wiley Interscience, Ed.) may be used.

In a very advantageous embodiment of the method according to the invention, the base is lithium diisopropylamide optionally combined with N,N,N',N'-tetramethylethylenediamine or 1,1,1,3,3,3-hexamethyldisilazane.

In another very advantageous embodiment of the method according to the invention, the reaction is carried out in a solvent chosen in particular from the group consisting of 1,2-dimethoxyethane (DME), tert-butyl methyl ether, tetrahydrofuran (THF), ether and mixtures thereof.

In a particularly advantageous embodiment of the invention, the β-ionone enolate of formula (5-a)

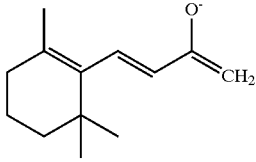
(5-a)

is reacted with the compound of formula (1-j)

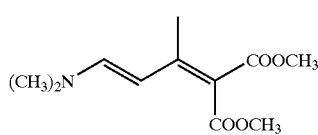
(1-j)

to give a compound of formula (6-a), in the form of a mixture of 2 isomers.

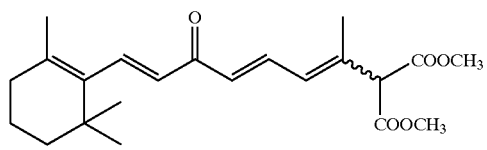
(6-a)

This derivative is treated with an organometallic derivative (for example CH$_3$MgBr) to give a compound of formula (7-a), in the form of a mixture of 2 isomers

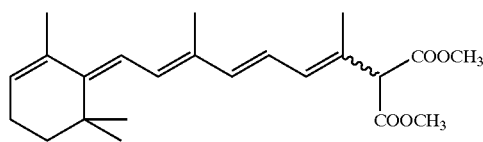
(7-a)

It is saponified, preferably with an aqueous-alcoholic solution of potassium hydroxide or of sodium hydroxide to give all-trans-retinoic acid of formula (8).

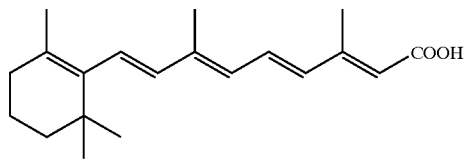
(8)

This acid is accompanied by its 13-Z isomer, in negligible proportions (<5%). The traces of 13-Z isomer are removed during crystallization of the all-trans-retinoic acid.

The subject of the present invention is also a method for preparing vitamin A:
  via the acid chloride of retinoic acid, according to methods known to persons skilled in the art, in particular according to the method described by Huisman et al., Recl. Trav. Chim. Pays-Bas (1956), 75, 977–1004,
  via the methyl or ethyl esters of retinoic acid, according to methods known to persons skilled in the art, in particular according to the method described by Wendler et al., J. Am. Chem. Soc. (1949), 71, 3267; Schwarzkoft et al., Helv. Chim. Acta (1949), 32, 443, 451–452; Ebeson et al., J. Am. Chem. Soc. (1955), 77, 4111–18), said method being characterized in that the retinoic acid is prepared according to the method described above.

The subject of the present invention is also the use of the compounds of formula (1) as intermediates in the synthesis of retinoids and carotenoids, in particular in the synthesis of retinoic acids and vitamin A.

The subject of the present invention is more specifically the use of the compound of formula (1-j) in the synthesis of retinoids and carotenoids.

In an advantageous embodiment according to the invention, the retinoid is chosen from the group consisting of retinoic acid, vitamin A (retinol), retinal, retinonitrile and etretinate.

The method according to the invention has many technical and economic advantages:
  the compounds of formula (1) are easily prepared, in one or two steps, from raw materials which are commercially available, which is not the case in the syntheses known from the literature or in industrial syntheses,
  the novel synthon enamino diester of formula (1-j) makes it possible to directly obtain, stereoselectively, all-trans-retinoic acid by a "one pot" multistep synthesis whose yield is greater than 60% (nonoptimized), and the preparation is carried out in a single day.

For the synthesis of vitamin A via all-trans-retinoic acid (via the corresponding acid chloride or esters), it can be carried out in two days, which is not the case for the industrial syntheses which are currently used.

Examples which follow illustrate the invention without however being limited to these particular embodiments.

Examples 1a to 1i relate to the preparation of the compounds of formula (1) containing (n+1) units from the compounds of formula (3) containing n units.

Examples 2a and 2c relate to the preparation of the compounds of formula (1) according to the second method.

Examples 3a to 3j illustrate the method for preparing the compounds of formula (3) which are useful for preparing the compounds of formula (1) containing n+1 or n+2 units, from the compounds of formula (1) containing n units according to Examples 1a to 1i.

Examples 4a to 4c illustrate the use of the compounds of formula (1) to prepare the corresponding aldehydes.

Examples 5 to 8 illustrate the synthesis of retinoids from the compounds of formula (1).

EXAMPLE 1

General Procedure for Preparing the Compounds of Formula 1 According to the First Method 15 mmol of DMFDMA are added to 10 mmol of diester, either in the cold state (dropwise), the reaction being monitored by thin-layer chromatography (TLC) and the product isolated by crystallization (protocol x), or at room temperature, the mixture then being heated directly to a temperature which makes it possible to remove by distillation the methanol formed; the reaction is monitored by thin-layer chromatography (TLC). At the end of the reaction, the DMFDMA in excess is removed by distillation under reduced pressure (protocol y).

EXAMPLE 1a

Synthesis of the Compound (1-a)

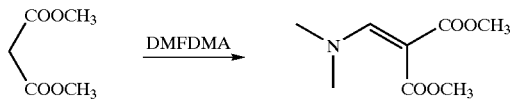

The synthesis is carried out according to protocol x. The product is obtained in the form of white crystals. Melting point=63° C. (ether).

EXAMPLE 1b

Synthesis of the Compound (1-j)

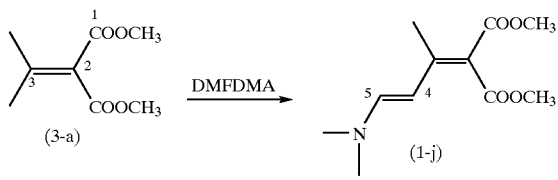

The synthesis is carried out according to protocol y. The enamino ester obtained is crystallized from pentane and the product is obtained in the form of beige crystals.

(Yield>85%). (rf: $CH_2Cl_2$, 0.15). m.p.: 113° C.

By carrying out the procedure in 50 ml of dimethylformamide (DMF) and adding 1 ml of trifluoroacetic acid, the time is brought to 1 h of boiling of DMF. Yield>85%.

IR: 1716; 1686; 1619; 1539; 1433; 1399; 1330; 1191; 1115; 1068; 995; 959. $^1H$ NMR ($CDCl_3$): 6.93 (d, 1H, J=13.2, $H_4$); 6.07 (d, 1H, J=13.2, $H_5$); 3.71 (s, 6H, $COOCH_3$); 2.91 (s, 6H, N—$(CH_3)_2$); 2.10 (s, 3H, 3-$CH_3$). $^{13}C$ NMR ($CDCl_3$) (CO); 167.3 (CH); 148.8; 97.4 ($CH_3$); 52.0; 51.9; 41.0; 16.7.

EXAMPLE 1c

Synthesis of the Compound (1-q) from (3, R=$R_1$=$CH_3$, Methyl Ester)

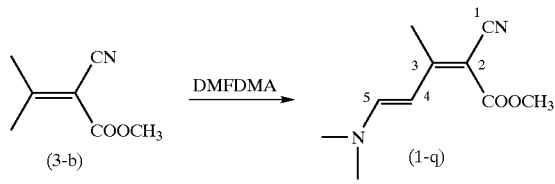

This product is synthesized according to a method derived from that described by Köechritz (already cited). 15.3 g (0.01 mol) of ethyl 2-cyano-3-methylcrotonate obtained according to the method described by Wideqvist (S. Acta Chem. Scand. (1949), 3, 303), 600 mg of acetic acid and 11.9 g (0.01 mol) of DMFDMA are mixed. The medium is heated for 2 h at 70° C. in order to remove the methanol and then at 100° C. The reaction is monitored by thin-layer chromatography (TLC) ($CH_2Cl_2$—MeOH 98: 2, rf: 0.7). The enamino ester is crystallized from ether and it is obtained in the form of yellow crystals.

(Yield>60%). m.p.: 85° C.

IR: 3145; 2180; 1696; 1615; 1526; 1403; 1273; 1238; 1185; 1137; 842. $^1H$ NMR ($CDCl_3$): 7.29 (d, 1H, J=13, $H_4$); 6.1 (d, 1H, J=13, $H_5$), 3.74 (s, 3H, $OCH_3$); 3.18 and 2.98 (2s, flattened, 6H), (t, 3H, N—$CH_3$); 2.30 (s, 3H, 3-$CH_3$).

EXAMPLE 1d

Synthesis of the Compound (1-c)

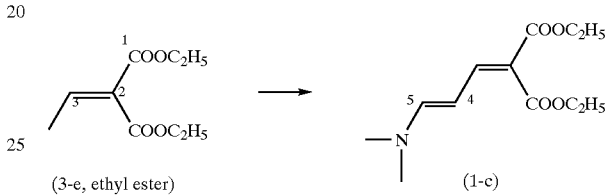

The synthesis is carried out according to the protocol y. The dimethylformamide (dimethyl acetal) in excess is distilled off under reduced pressure and the enamino ester obtained is crystallized from ether. The product is obtained in the form of orange yellow crystals.

(Yield>75%). (rf: $CH_2Cl_2$, 0.15). m.p.: 44° C.

IR: 1684; 1654; 1618; 1555; 1395; 1378; 1218; 1174; 1117; 1071; 1030; 1014. $^1H$ NMR ($CDCl_3$): 7.75 (d, 1H, J=12.5, $H_5$); 6.94 (d, 1H, J=12.5, $H_3$); 6.11 (t, 1H, J=12.5, $H_4$); 4.28 and 4.20 (2q, 4H, $CH_2$); 3.01 (bs, 6H, N—$(CH_3)_2$); 1.33 (2q, 6H, $CH_3$). $^{13}C$ NMR ($CDCl_3$) (CO); 167.1 and 166.9 (CH); 157.0; 154.0; 97.5 ($CH_2$); 60.4; 60.2 ($CH_3$) 14.8; 14.6.

EXAMPLE 1e

Synthesis of the Compound (1-k)

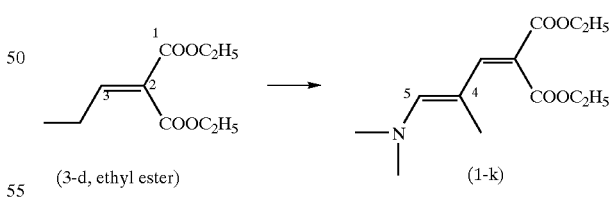

The synthesis is carried out according to the protocol y. The dimethylformamide (dimethyl acetal) in excess is distilled off under reduced pressure and the enamino ester obtained is crystallized from ether. The product is obtained in the form of orange yellow crystals.

(Yield>75%). (rf: $CH_2Cl_2$, 0.15). m.p.: 44° C. IR: 1724; 1678; 1619; 1536; 1426; 1390; 1371; 1233; 1169; 1126; 1082; 1023; 918; 881; 761; 726. $^1H$ NMR ($CDCl_3$) : 7.31 (s, 1H, $H_5$); 6.79 (s, 1H, $H_3$); 3.82 and 3.75 (2s, 6H, N—$(CH)_3$); 3.08 (s, 6H, $OCH_3$); 1.83 (s, 3H, $CH_3$). $^{13}C$ NMR ($CDCl_3$); $CH_3$:51.8; 51.5; 43.3.

EXAMPLE 1f

Synthesis of the Compound (1-p)

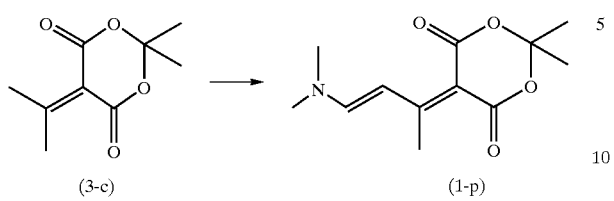

(3-c)  (1-p)

The synthesis is carried out according to the protocol y. The dimethylformamide (dimethyl acetal) in excess is distilled off under reduced pressure and the enamino ester obtained is crystallized from ethyl acetate. The product is obtained in the form of orange-colored crystals.

(Yield>80%). (rf: $CH_2Cl_2$, 0.15). m.p.: 152° C. IR: 3374; 3415; 1700; 1671; 1596; 1518; 1394; 1318; 1252; 1218; 1199; 1110; 959. $^1$H NMR ($CDCl_3$): 7.65 and 7.40 (2d, 2H, J=12.8, $H_{5,4}$); 3.27 and 3.08 (2s, 6H, N—$(CH_3)_2$); 2.54 (s, 3H, 3-$CH_3$) 1.66 (s, 6H, $CH_3$). $^{13}$C NMR ($CDCl_3$); CO: 169.5; CH; 103.6; $CH_3$; 46.6; 36.6; 27.0; 19.2.

EXAMPLE 1g

Synthesis of the Compound (1-s)

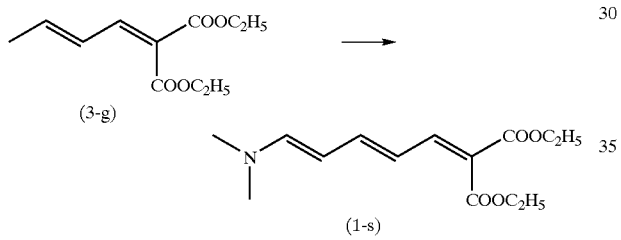

(3-g)

(1-s)

The synthesis is carried out according to the protocol y. The dimethylformamide (dimethyl acetal) is distilled off under reduced pressure. The product is obtained in the form of an orange yellow oil. Yield>75%.

IR: 1725; 1633; 1541; 1375; 1213; 1151; 1100; 1062; 860. $^1$H NMR ($CDCl_3$): 7.53 (d, 1H, J=12.3, $H_3$); 6.85–6.50 (m, 3H, $H_4$+$H_5$+$H_7$); 5.23 (m, 1H, $H_6$); 4.25 (2q, 4H, $CH_2$); 2.92 (S, 6H, N—$(CH)_3$); 1.33 (2t, 6H, $CH_3$). $^{13}$C NMR ($CDCl_3$) (CO) 166.6 and 166.3 (CH) 151.1; 151.0; 116 4; 110.0; 99.7 ($CH_3$); 14.7.

EXAMPLE 1h

Preparation of the Compound (1-t)

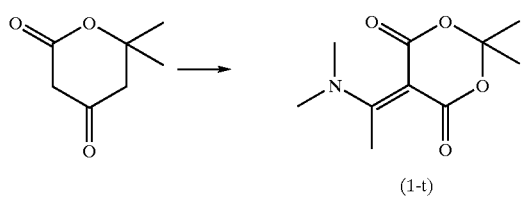

(1-t)

The synthesis is carried out according to the protocol y with dimethylacetamide (dimethyl acetal). The dimethylac- etamide (dimethyl acetal) is distilled off under reduced pressure. The product is obtained in the form of a crystallized red product. Yield>50%.

$^1$H NMR ($CDCl_3$): 3.48 (s, 3H, $CH_3$); 3.23 (s, 6H, N—$(CH)_3$); 1.71 (s, 6H, $C(CH_3)_2$).

EXAMPLE 1i

Synthesis of the Compound (1-u)

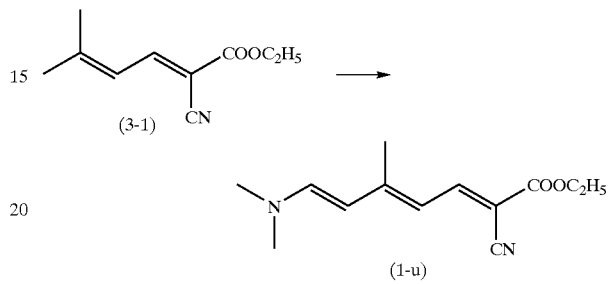

(3-1)

(1-u)

The synthesis is carried out according to the protocol y. Yield>40%.

IR: 2925; 2200; 1707; 1691; 1627; 1516; 1432; 1235; 1182; 1109; 1089; 1019. $^1$H NMR ($CDCl_3$): 8.18 (d, 1H, J=13.2); 7.04 (d, 1H, J=13); 6.38 (d, 1H, J=13.2); 5.38 (d, 1H, J=13); 3.83 (s, 3H); 3.03 (s, 6H); 1.59 (s, 3H). $^{13}$C NMR ($CDCl_3$) (CO) 165.7; (CN) 114.7; (CH) 151.0; 481.5; 117.7; 114.7 ($CH_3$); 52.0; 13.9.

EXAMPLE 2

General Procedure for Preparing the Compounds of Formua (1) According to the Second Method

EXAMPLE 2a

Preparation of the Compound (1-v)

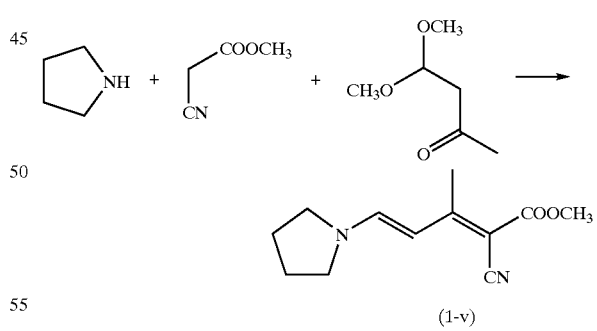

(1-v)

Under argon, 11 mmol of methyl cyanoacetate, 10 mmol of acetylacetaldehyde dimethyl acetal and 12 mmol of pyrrolidine in 100 ml of toluene are stirred for 1 h at room temperature and then under reflux for 6 h with a Dean-Stark type apparatus. The product crystallizes on cooling and is recrystallized from an ether-methanol mixture. Yellow crystals m.p. 162–64° C. Yield>65%.

IR: 3460; 2965; 2189; 1679; 1570; 1454; 1230. $^1$H NMR ($CDCl_3$): 8.07 (d, 1H, J=13.5); 5.56 (d, 1H, J=13.5); 3.77 (s, 3H); 3.59 (m, 2H); 3.46 (m, 2H); 2.25 (s, 3H); 2.05 (m, 4H).

$^{13}$C NMR (CDCl$_3$) (CO) 166.6 (CH) 152.9; 97.9; CN 82.7; (CH$_2$) 49.7; 49.1; 25.1; 24.7 (CH$_3$); 51.6; 16.7.

EXAMPLE 2b

Preparation of the Compound (1-w)

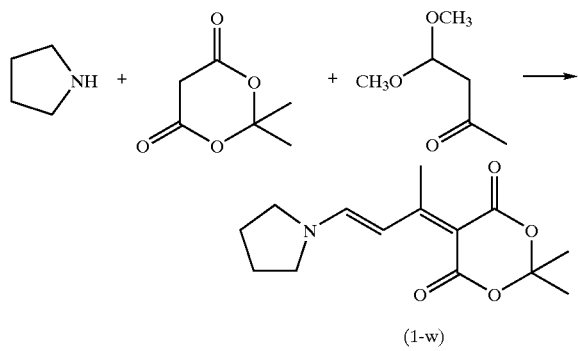

(1-w)

Under argon, 11 mmol of Meldrum's acid, 10 mmol of acetylacetaldehyde dimethyl acetal and 12 mmol of pyrrolidine in 100 ml of toluene are stirred for 1 h at room temperature and then under reflux for 6 h with a Dean-Stark type apparatus. The product crystallizes on cooling and is recrystallized from an ether-methanol mixture. Red crystals m.p. 218–22° C. (dec). Yield>35%.

IR: 3440; 2978; 1668; 1558; 1359; 1188. $^1$H NMR (CDCl$_3$): 8.24 (d, 1H, J=14); 7.05 (d, 1H, J=14); 3.68 (m, 4H); 2.36 (s, 3H); 2.08 (m, 4H); 1.70 (s, 6H). $^{13}$C NMR (CDCl$_3$) (CO) 166.9; 166.1 (CH) 152.0; 103.8; (CH$_2$) 50.5; 50.1; 24.9; 24.5 (CH$_3$); 25.8; 16.5.

EXAMPLE 2c

Synthesis of the Compound (1-q) According to the Preceding Method with Dimethylamine Instead of Pyrrolidine

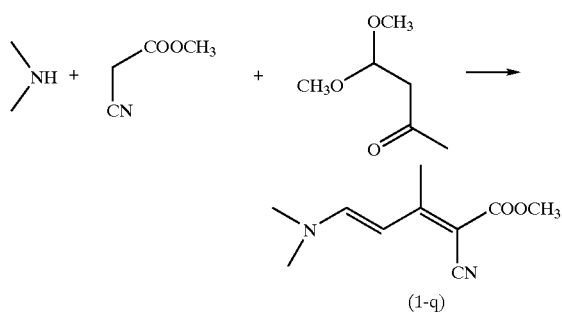

(1-q)

The enamino ester is crystallized from ether and it is obtained in the form of yellow crystals. (Yield>50%).

EXAMPLE 3a

First Method (n Units to n+1 Units)

Under argon, 10 mmol of an alkylmagnesium halide, for example methylmagnesium chloride or bromide (3 M in tetrahydrofuran (THF)) are added at a temperature in the region of −10° C., to 10 mmol of enamine (1) comprising n units, for example the compound (1-j) in 20 ml of THF. The medium is left at room temperature for 1 h 30 min. The medium is cooled to around −0° C. and 1 ml of ethanol is added. The medium is slightly acidified with 1 M HCl and the impurities are extracted with ether. A basic medium is obtained by adding aqueous ammonia, at around 0° C. The medium is extracted with dichloromethane, washed with water and dried over sodium sulfate. The crude product is dissolved in 15 ml of toluene and heated for 30 min at boiling temperature. After evaporation under reduced pressure, the product is isolated. This product, treated with DMFDMA, makes it possible to prepare the compound of formula (1) comprising n+1 units.

EXAMPLE 3b

Second Method (n Units to n+2 Units)

Under argon, 10 mmol of butyllithium are added at a temperature in the region of −25° C., to 10 mmol of diisopropylamine in 20 ml of THF. 10 mmol of ketone, in particular acetone, in 15 ml of THF, are slowly added. The stirring is maintained for 10 min, and 10 mmol of enamine (1) comprising n units or of enol ether (1) comprising n units, in 20 ml of THF, are added at around −30° C. The temperature is allowed to return to room temperature over 10 minutes and the medium is heated for 2 h 30 min under reflux (until the emission of dimethylamine ceases). The medium is cooled to a temperature between −10 and 0° C. and 20 mmol of methylmagnesium chloride (3 M in THF) are added. The reaction is allowed to return to room temperature. After stirring for 1 h 30 min, 1 ml of ethanol is added, at 0° C., and then the medium is acidified with 1 M HCl. It is extracted with dichloromethane, washed with 1 M HCl and then with water. After drying over MgSO$_4$, the product is isolated after distillation of the solvents under reduced pressure. This product, treated with DMFDMA, makes it possible to prepare the compound of formula (1) comprising n+2 units.

EXAMPLE 3c

Synthesis of the Compound (3-f)

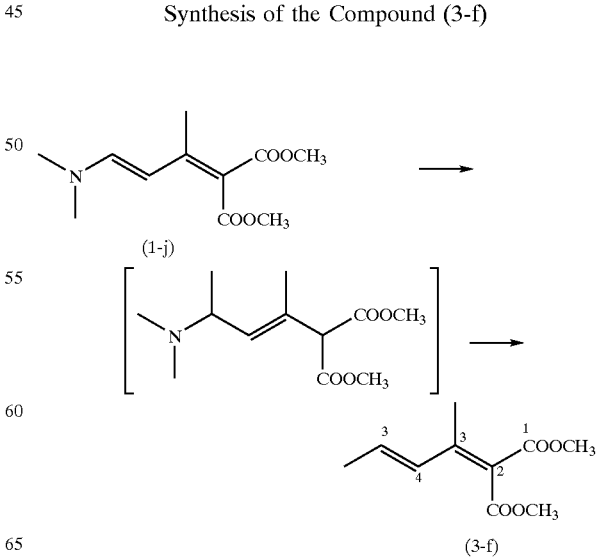

(3-f)

Starting with the compound (1-j), the method of Example 3a is used.

Colorless oil. Yield 90%.

IR: 2960; 1723; 1638; 1591; 1435; 1307; 1224; 1065. $^1$H NMR (CDCl$_3$): 6.77 (dq, 1H, J=15.5, j'=1.6, H$_4$); 6.32 (dq, 1H, J=15.5, j'=6.8, H$_5$); 3.77 and 3.78 (2s, 6H, COOCH$_3$); 2.15 (s, 3H, 3-CH$_3$); 1.89 (dd, 3H, J=6.8, J'=1.6, 5-CH$_3$). $^{13}$C NMR (CDCl$_3$): (CO); 166.2; 166.1 (CH); 136.4; 129.6 (CH$_3$); 52.4; 52.1; 19.1; 16.0.

EXAMPLE 3d

Synthesis of the Compound (3-e) (Example 5)

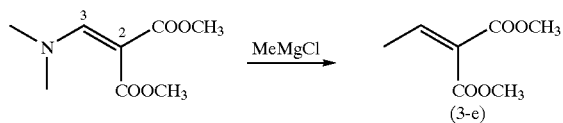

Starting with the compound prepared in Example 2, the method of Example 3a is used.

Rapid chromatography on silica rf: 0.8 (eluent: dichloromethane). Colorless oil Yield purified (80%).

IR (film): 2955; 1734; 1646; 1437; 1382; 1359; 1265; 1225; 1128; 1056. $^1$H NMR (CDCl$_3$): 7.10 (q, 1H, J=7.3, H$_3$); 3.80 (2s, 6H, OCH$_3$); 1.93 (d, 3H, J=7.3 4-CH$_3$). $^{13}$C NMR (CDCl$_3$) (CO); 165.6; 164.2 (CH); 145.6 (CH2); 61.0 (CH$_3$); 52.3; 15.5.

EXAMPLE 3e

Synthesis of the Compound (3-g)

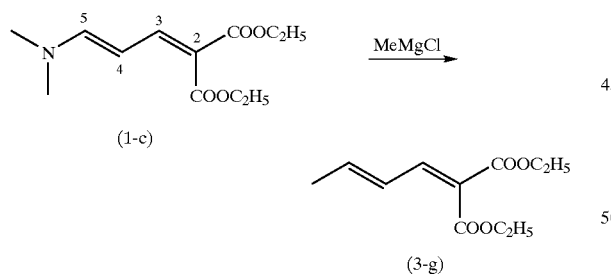

Starting with the compound (1-c), the method of Example 3a is used.

Rapid chromatography on silica rf: 0.8 (eluent: dichloromethane). Colorless oil Yield purified (80%). Mixture of isomers (1 very predominant, >95%).

IR (film): 2984; 2939; 1725; 1641; 1604; 1447; 1373; 1300; 1242; 1213; 1170; 1095; 1024; 979. $^1$H NMR (CDCl$_3$): 7.35 (d, 1H, J=11.5, H$_3$); 6.51 (dd, 1H, J=11.5, J=1.7 H$_4$); 6.35 (m, 1H, H$_5$); 4.30 (2q, 2H, J=7.2, CH$_2$); 1.91 (d, 3H, J=6.8 6-CH$_3$); 1.32 (2t, 3H, J=7.2, CH$_3$); $^{13}$C NMR (CDCl$_3$) (CO); 165.3; 164.7 (CH); 145.0; 144.2; 127.0 (CH2); 61.0 (CH$_3$); 19.0; 14.0.

EXAMPLE 3f

Synthesis of the Compound (3-h)

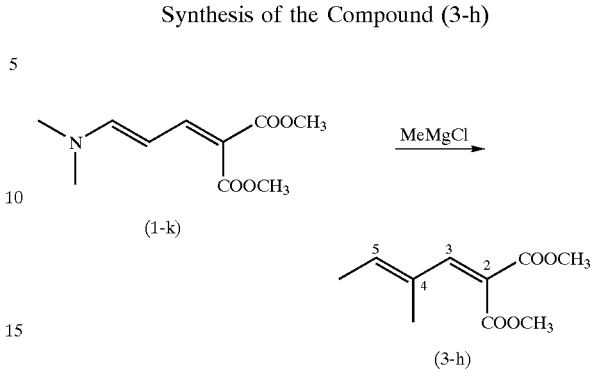

Starting with the compound (1-k), the method of Example 3a is used.

Rapid chromatography on silica rf: 0.8 (eluent: dichloromethane); Colorless oil Yield purified (80%).

IR (film): 2953; 1735; 1622; 1607; 1436; 1374; 1263; 1221; 1074; 1038. $^1$H NMR (CDCl$_3$): 7.25 (s, 1H, H$_3$); 6.11 (q, 1H, J=7.1, H$_5$); 3.79 and 3.74 (2s, 6H, OCH$_3$) 1.78 (d, 3H, J=7.1, 6-CH$_3$); 1.70 (s, 3H, 4-CH$_3$). $^{13}$C NMR (CDCl$_3$) (CO); 167.5; 165.0 (CH); 147.1; 140.8 (CH$_3$); 52.2; 14.6; 12.1.

EXAMPLE 3g

Synthesis of the Compound (3-i)

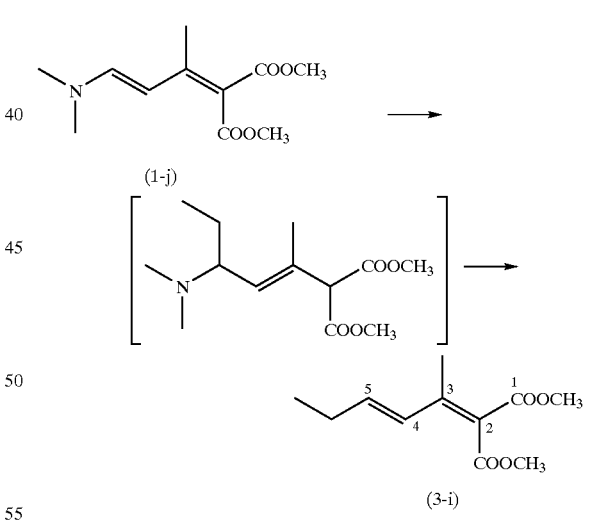

Starting with the compound (1-j), the method of Example 3a is used.

Rapid chromatography on silica rf: 0.8 (eluent: dichloromethane. Colorless oil. Yield 90%.

$^1$H NMR (CDCl$_3$): 6.77 (dt, 1H, J=15.5, j'=1.5, H$_4$); 6.34 (dt, 1H, J=15.5, j'=6.7, H$_5$); 3.80 and 3.78 (2s, 6H, COOCH$_3$); 2.22 (2dq, 2H, CH$_2$, J=7.5, J=1.5); 2.17 (s, 3H, 3-CH$_3$); 1.06 (t, 3H, J=7.5, 6-CH$_3$). $^{13}$C NMR (CDCl$_3$): (CO); 166.3; 166.1 (CH); 142.9; 127.3 (CH$_2$); 26.4 (CH$_3$); 52.1; 52.0; 16.0; 12.9.

EXAMPLE 3h

Synthesis of the Compound (3-j)

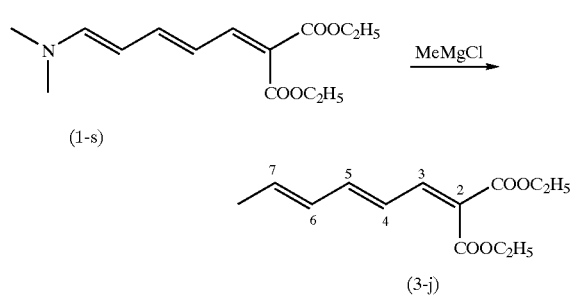

Starting with the compound obtained in Example 1g, the method of Example 3a is used.

Rapid chromatography on silica rf: 0.8 (eluent: dichloromethane). Colorless oil Yield purified (80%).

IR (film): 2953; 1734; 1700; 1622; 1607; 1436; 1373; 1263; 1222; 1075; 1038. $^1$H NMR (CDCl$_3$): 7.37 (d, 1H, J=11.6, H$_3$); 6.64 (m, 1H, H$_5$); 6.56 (m, 1H, H$_4$); 6.18 (m, 1H, H$_6$); 6.05 (m, 1H, H$_7$); 4.24 (2q, 2H, J=7.1, CH$_2$); 1.84 (d, 3H, J=6.8, 6-CH$_3$); 1.32 (2t, 3H, J=7.1, CH$_3$). $^{13}$C NMR (CDCl$_3$) (CO); 165.3; 164.7 (CH); 145.3; 145.0; 137.6; 131.3; 123.8 (CH2); 61.0 (CH$_3$); 18.6; 14.0.

EXAMPLE 3i

Synthesis of the Deconjugated Isomer of the Compound (3-k) (Methyl Ester)

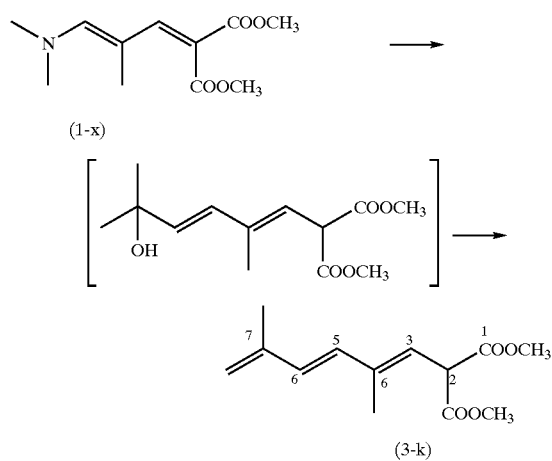

Starting with the compound (1-x), the method of Example 3b is used.

Colorless oil. Yield 60%.

IR: 2954; 1740; 1738; 1640; 1610; 1435; 1311; 1259; 1224; 1195; 1149; 1021; 962. $^1$H NMR (CDCl$_3$): 6.38 (d, 1H, J=16, H$_5$); 6.29 (d, 1H, J=16, H$_6$); 5.81 (d, 1H, J=9.6, H$_3$); 5.03 (2s, 2H, CH$_2$); 4.44 (d, 1H, J=9.6, H$_2$); 3.75 (s, 6H, COOCH$_3$); 1.88 (s, 3H, 7-CH$_3$); 1.86 (s, 3H, 4-CH$_3$). $^{13}$C NMR (CDCl$_3$): (CO); 168.4 (CH); 132; 131.8; 122.2; 51.4; (CH$_2$); 117.3 (CH$_3$); 52.7; 18.4; 18.0.

EXAMPLE 3j

Synthesis of the Compound (3-l)

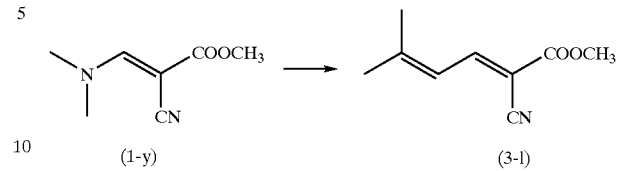

The compound (1-y) is obtained according to the technique used by H. Merwein *Justus Liebigs Ann. Chem.* 1961, 641, 1–39. Starting with it, the compound (3-l) is obtained according to the method described in Example 3b.

Beige crystals Yield>40%). m.p. 64–66° C.

IR (film): 2958; 2220; 1748; 1724; 1620; 1575; 1437; 1264; 1163; 1093; 762. $^1$H NMR (CDCl$_3$): 8.16 (d, 1H, J=12.3); 6.52 (d, 1H, J=12.3); 3.89 (s, 3H); 2.06 (s, 3H); 2.02 (s, 3H). $^{13}$C NMR (CDCl$_3$) (CO); 163.3; 114.6 (CN); (CH); 151.5; 122.7 (CH$_3$); 52.8, 6; 27.4; 20.0.

EXAMPLE 4a

Method of Converting a Compound of Formula (1-x) to the Corresponding Aldehyde (4-a)

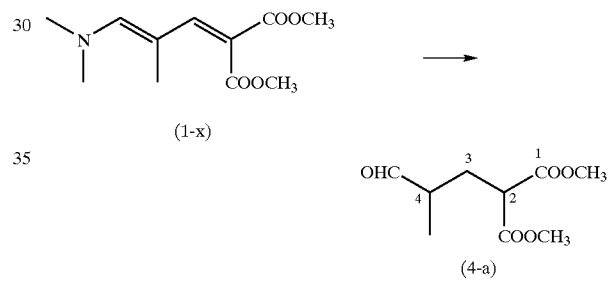

0.01 mol of enamino ester (1-x) in 40 ml of dichloromethane and 40 ml of 1 M HCl are stirred for 6 h at room temperature. The organic phase is washed with water and dried over MgSO$_4$. After distillation of the dichloromethane under reduced pressure, a colorless oil is obtained. Yield 95%.

IR: 3006; 2958; 2847; 1739; 1695; 1649; 1599; 1437; 1317; 1264; 1219; 1154; 1017. $^1$H NMR (CDCl$_3$): 9.49 (s, 1H, CHO); 6.72 (dq, 1H, J=9.4, J'=1.4, H$_3$); 4.54 (d, 1H, J=9.4, H$_2$); 3.78 (s, 6H, CH$_3$); 1.79 (d, 3H, 4-CH$_3$). $^{13}$C NMR (CDCl$_3$); (CO); 193.9 (CH); 141.6; 53.1; (CH$_3$); 51.5; 9.5.

EXAMPLE 4b

Method for Converting a Compound of Formula (1-j) to the Corresponding Aldehydes (4-b) and (4-c)

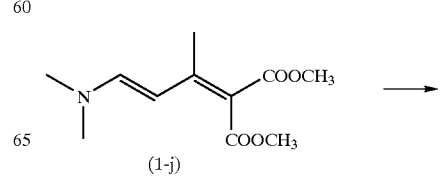

-continued

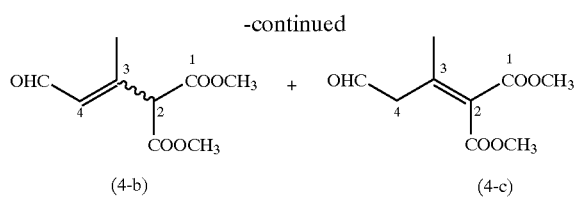

a) 0.01 mol of enamino ester in 40 ml of dichloromethane and 40 ml of 2 M HCl are stirred for 15 h at room temperature. The organic phase is washed with water and dried over MgSO$_4$. After distillation of the dichloromethane under reduced pressure, a colorless oil consisting of 3 isomers is obtained. Yield 95%.

b) 0.01 mol of enamino ester in suspension in 40 ml of cyclohexane and 10 ml of formic acid are stirred for 2 h at room temperature. 100 ml of ice-cold water are added and the aqueous phase is extracted with ether. The organic phases are washed with water and dried over MgSO$_4$. After distillation of the solvents under reduced pressure, a colorless oil consisting of 3 isomers is obtained Yield= (50%).

EXAMPLE 4c

Method for Converting a Compound of Formula (1-u) to the Corresponding Aldehyde (4-d)

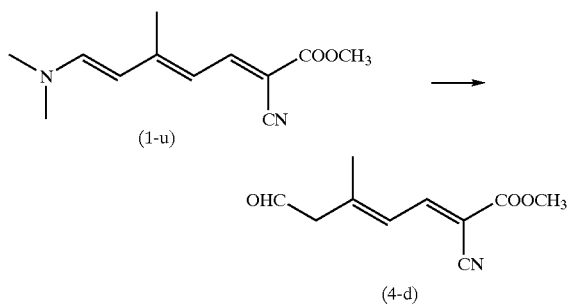

0.01 mol of enamino ester in 40 ml of dichloromethane and 40 ml of 2 M HCl are stirred for 18 h at room temperature. The organic phase is washed with water and dried over MgSO$_4$. After distillation of the dichloromethane under reduced pressure, a colorless oil is obtained. Yield>25%.

IR (film): 2958; 2225; 1734; 1691; 1580; 1436; 1264; 1087; 1015; 801; 703. $^1$H NMR (CDCl$_3$): 9.73 (s, 1H); 8.32 (d, 1H, J=12); 7.33 (d, 1H, J=12); 3.97 (s, 3H); 3.35 (s, 2H); 2.09 (s, 3H). $^{13}$C NMR (CDCl$_3$) (CO); 193.4; (CH); 147.8; 137.8 (CH$_2$); 53.5 (CH$_3$); 53.6, 6; 10.9.

EXAMPLE 5

General Method for Synthesizing Retinoids

Under argon, 10 mmol of butyllithium are added at a temperature in the region of 25° C. to 10 mmol of diisopropylamine in 20 ml of dimethoxyethane (DME). 10 mmol of β-ionone in 20 ml of DME are slowly added at a temperature between −30 and −40° C. The stirring is maintained for 20 minutes and 10 mmol of the derivative (1), in which G represents a group —NR$_4$R$_5$ or OP, in 50 ml of DME are added. The medium is allowed to return to room temperature over 10 minutes and it is heated for 1 h under reflux (until the emission of dimethylamine ceases). The medium is cooled to a temperature between −10 and 0° C. and 20 mmol of alkyl- or arylmagnesium halide (3 M in THF) ae added. The medium is allowed to return to room temperature over 30 minutes and 15 ml of ethanol and then 5 equivalents of potassium hydroxide in 50 ml of water are added at 0° C. The medium is stirred for 30 minutes at room temperature and for 45 minutes at 40° C. The organic solvents are distilled off under reduced pressure. The medium is acidified with a 2 N ice-cold hydrochloric acid solution. It is extracted with ethyl acetate, washed with 1 M hydrochloric acid and then washed with water and dried over sodium sulfate.

EXAMPLE 6

"One Pot" Synthesis of Retinoic Acid (3,7-dimethyl-9-(2,6,6-trimethylcyclohex-1-enyl)nona-2,4,6,8-tetraenoic acid)

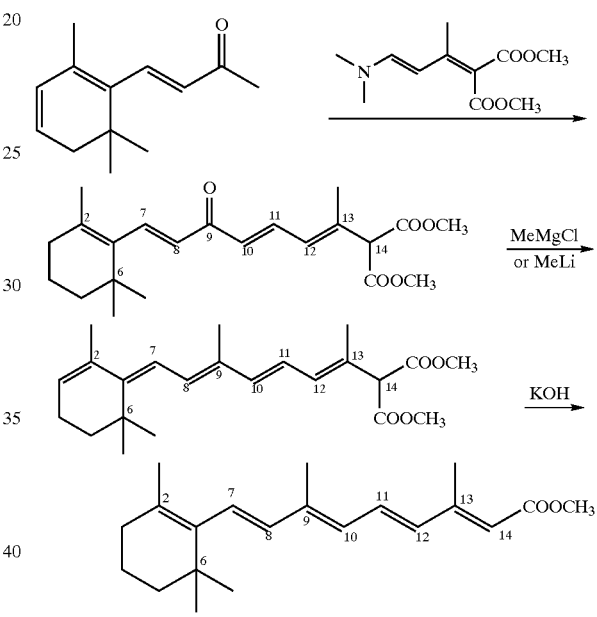

The β-ionone is reacted with the compound (1-j) prepared in Example 1b according to the general method described in Example 5.

The yield after purification is equal to 61%.

The physicochemical characteristics are identical to those of a reference sample (SIGMA).

EXAMPLE 7

Preparation of the 9,12-dimethyl Analog of All-Trans-Retinoic Acid (4,7-dimethyl-9-(2,6,6-trimethylcyclohex-1-enyl)nona-2,4,6,8-tetraenoic acid)

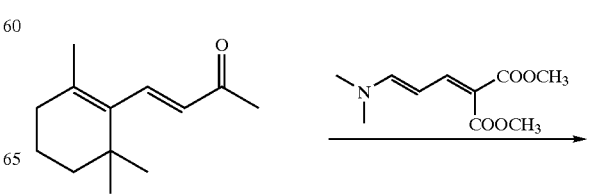

-continued

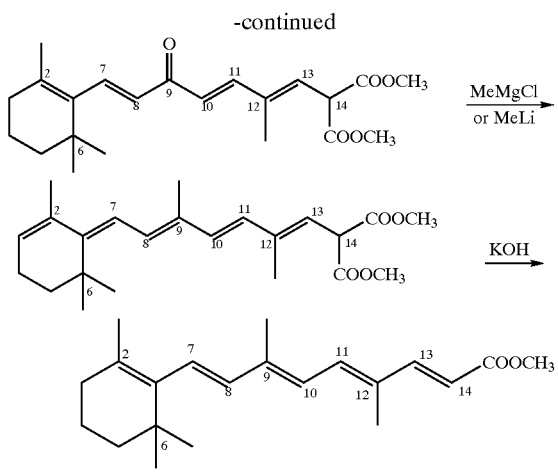

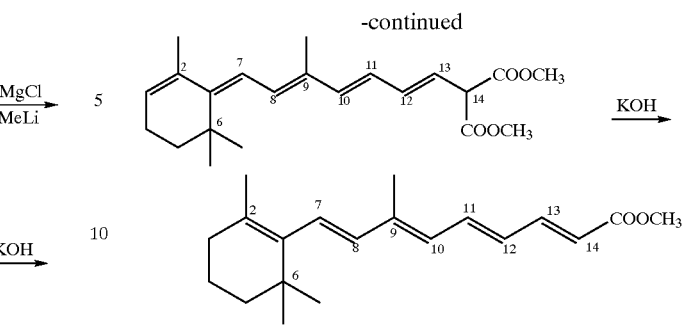

The β-ionone is reacted with the compound (1-x) according to the general method described in Example 5. TLC: rf: 0.3 (CH$_2$Cl$_2$/MeOH 95/5).

The yield of crude product is equal to 75%.

The crude product is extracted with a saturated bicarbonate solution. After acidification and extraction with ether, the product is purified by chromatography on silica and obtained in the form of a yellow liquid.

The yield of purified product is equal to 25%.

IR: 2948; 2850; 1715; 1601; 1500; 1460; 1028; 756; 697.
$^1$H NMR (CDCl$_3$): 7.53 (d, 1H, J=15.4, H$_{13}$); 6.83 (d, 1H, J=12.1, H$_{13}$); 6.38 (m, 2H, H$_{7+10}$); 6.23 (d, 1H, J=15.1, H$_8$); 5.87 (d, 1H, J=15.4, H$_{14}$): 2.03 (s, 3H, 12-CH$_3$); 1.95 (s, 3H, 9-CH$_3$); 1.94 (m, 2H, 3-CH$_2$); 1.80 (s, 2H, 4-CH$_2$); 1.75 (s, 3H, 3-CH$_3$); 1.67 (m, 2H, 5-CH$_2$); 1.05 (s, 3H, 6-CH$_3$). $^{13}$C NMR (CDCl$_3$) (CO); 185.6 (CH); 151.6; 137.6; 137.4; 136.1; 130.3; 125.4 (CH$_2$); 39.5; 34.2; 19.1 (CH$_3$); 30.9; 28.9; 12.7.

EXAMPLE 8

Preparation of the 13-Demethyl Analog of Retinoic Acid (7-methyl-9-(2,6,6-trimethylcyclohex-1-enyl) nona-2,4,6,8-tetraenoic acid)

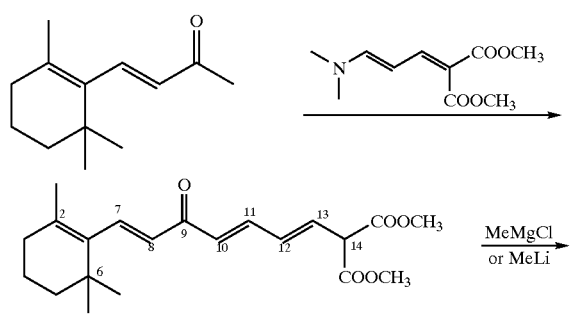

The general method described in Example 5 is used. TLC: rf: 0.35 (CH$_2$Cl$_2$/MeOH 95/5). Yield after purification 7 g (52%).

The product is obtained in the form of a mixture of isomers in which the all-trans isomer is very predominant.

What is claimed is:
1. A compound of the formula:

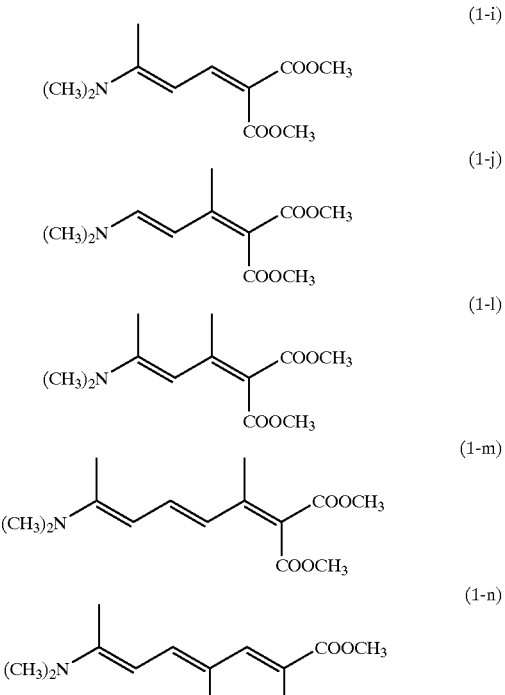

or an ethyl ester analog thereof.

* * * * *